United States Patent [19]

Aliahmad et al.

[11] Patent Number: 5,295,960
[45] Date of Patent: Mar. 22, 1994

[54] CATHETER WITH INTERIOR BALLOON

[75] Inventors: Wassim Aliahmad, Irvine; Said S. Hilal, Laguna Niguel, both of Calif.

[73] Assignee: Applied Medical Resources Corporation, Laguna Hills, Calif.

[21] Appl. No.: 861,474

[22] Filed: Apr. 1, 1992

[51] Int. Cl.$^5$ .............................. A61M 29/00
[52] U.S. Cl. ...................... 604/96; 604/103; 606/192
[58] Field of Search .............. 604/96, 97, 101, 103; 606/192–196

[56] References Cited

U.S. PATENT DOCUMENTS

| | | | |
|---|---|---|---|
| 1,852,351 | 4/1932 | Lewis | 604/96 |
| 3,438,375 | 4/1969 | Ericson . | |
| 3,866,599 | 2/1975 | Johnson . | |
| 4,217,903 | 8/1980 | Witherow . | |
| 4,240,433 | 12/1980 | Bordow | 604/96 |
| 4,254,774 | 3/1981 | Boretos . | |
| 4,301,797 | 11/1981 | Pollack | 604/101 |
| 4,773,393 | 9/1988 | Haber et al. | 606/195 |
| 4,823,812 | 4/1989 | Eshel et al. . | |
| 4,913,701 | 4/1990 | Tower . | |
| 4,950,238 | 8/1990 | Sullivan | 604/101 |
| 5,036,868 | 8/1991 | Berggren et al. . | |
| 5,092,873 | 3/1992 | Simpson et al. | 604/101 |

FOREIGN PATENT DOCUMENTS 1239432 4/1967 Fed. Rep. of Germany ...... 606/194

Primary Examiner—John D. Yasko
Assistant Examiner—Anthony Gutowski
Attorney, Agent, or Firm—Richard L. Myers

[57] ABSTRACT

A catheter includes a body having tubular walls defining a lumen extending along an axis from the distal end of the body to a proximal end of the body. Portions of the walls define at least one balloon hole extending from the lumen through the walls of the body. Elastomeric material restrained to the hole defining portions interiorly of the body expand outwardly of the (catheter) body to form a balloon when the lumen is pressurized with fluid. The elastomeric material my take the form of a patch or a full lining of the catheter walls defining the lumen. A method for making the catheter includes the step of retaining portions of an elastomeric layer around the hole interiorly of the lumen. A preferred method of manufacturing the catheter includes the step of providing the catheter body and an inner layer of elastomeric sheet material simultaneously in a co-extruder.

5 Claims, 4 Drawing Sheets

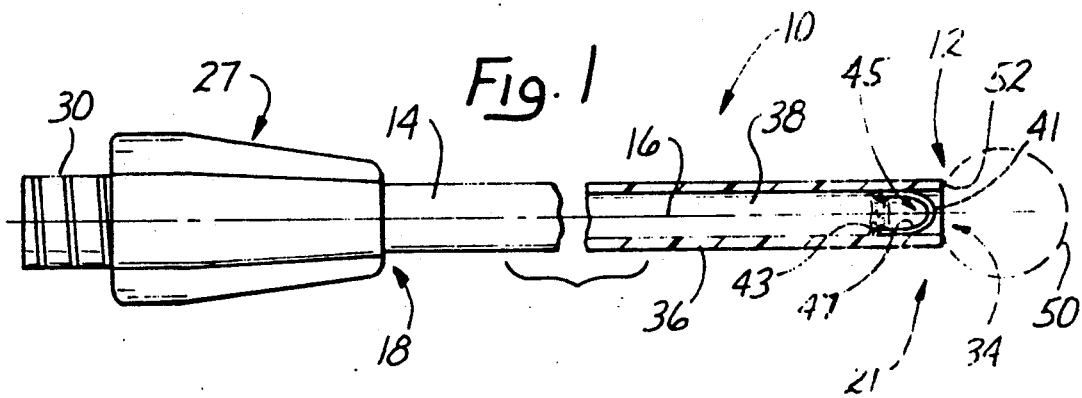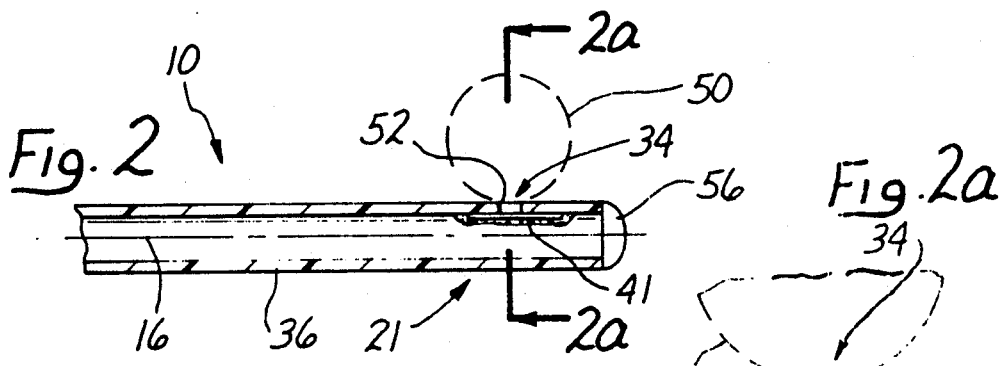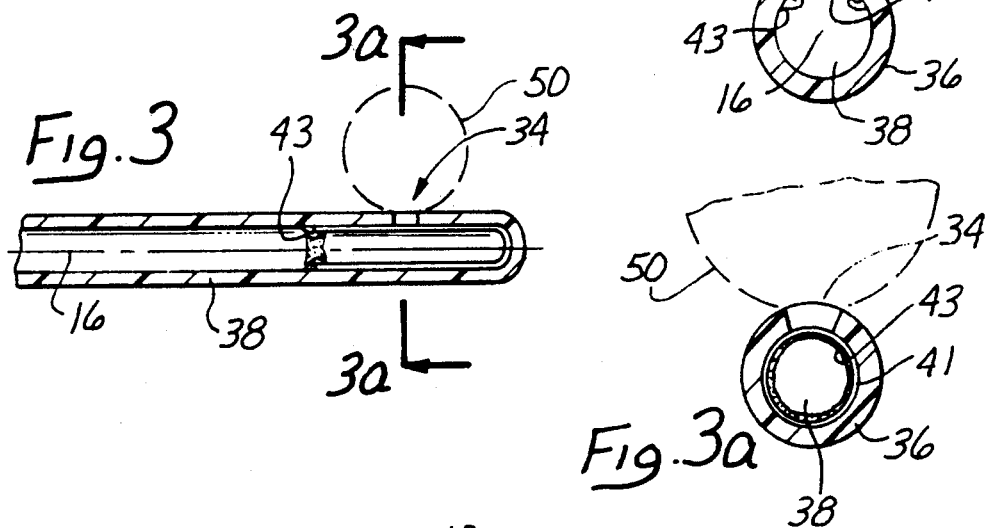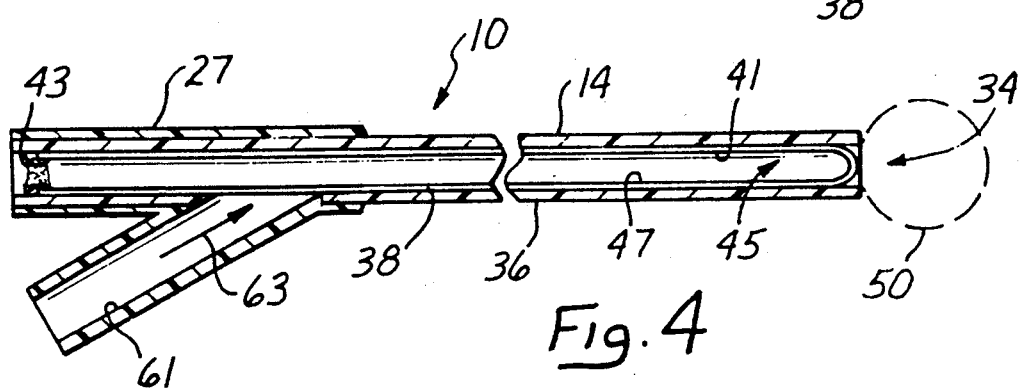

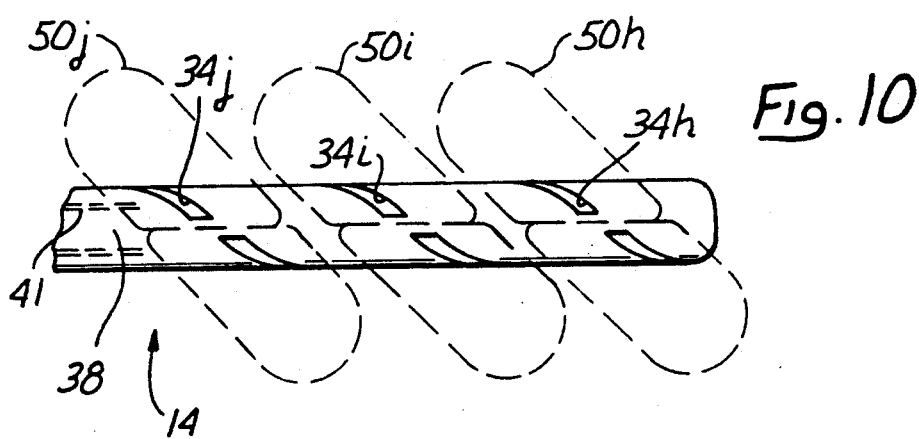
Fig. 10
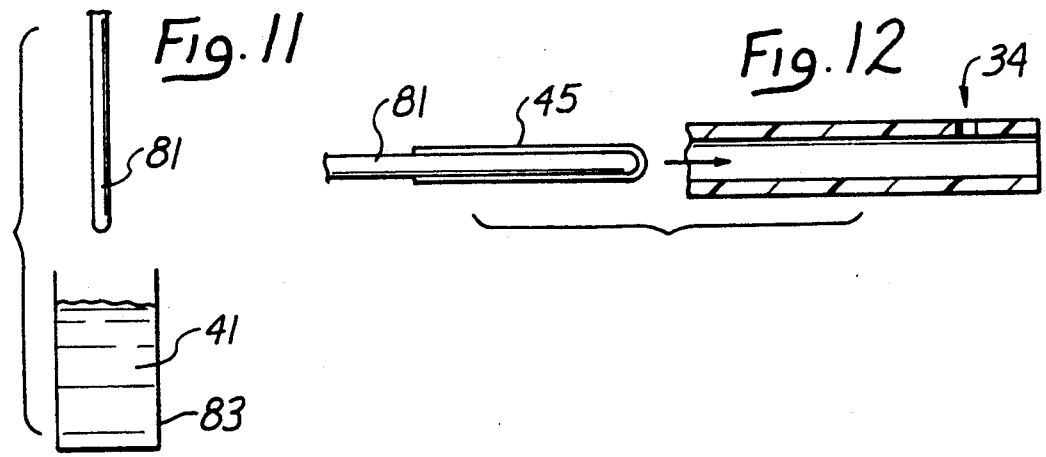
Fig. 11
Fig. 12
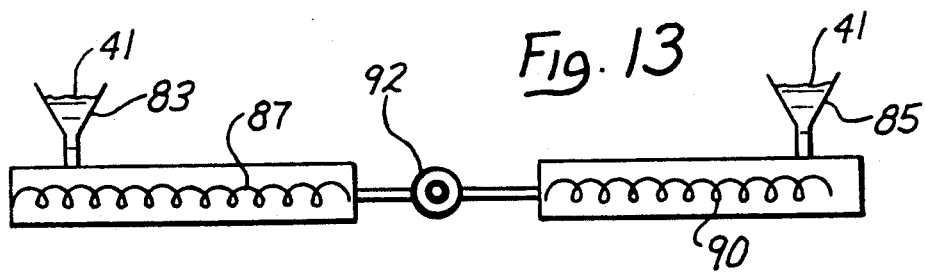
Fig. 13
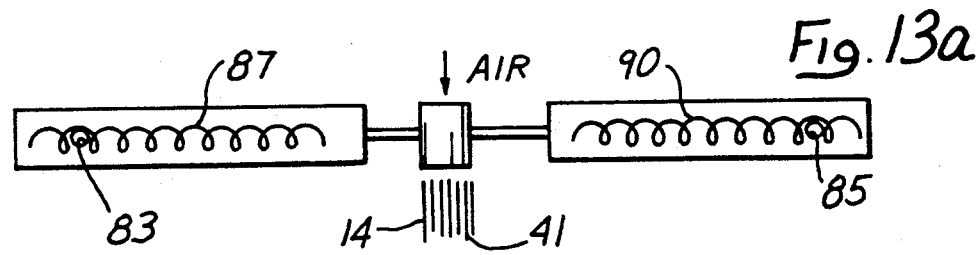
Fig. 13a

CATHETER WITH INTERIOR BALLOON

BACKGROUND OF THE INVENTION

1. Field of the Invention

This invention relates generally to catheters adapted for use in surgical procedures and more specifically to catheters having inflatable balloons.

2. Discussion of the Prior Art

In many surgical procedures it is desirable to introduce an elongate flexible object into a body conduit and to enlarge the distal end of that object at an operative site. Catheters are well known to perform this function, and in one common variety a balloon is disposed at the distal end of the catheter to provide for the desired enlargement. When this balloon is inflated, it typically exceeds the radial diameter of the catheter.

Several surgical procedures, such as embolectomy and angioplasty procedures, take advantage of this balloon catheter construction. In an embolectomy procedure, the distal end of the catheter is introduced beyond a thrombus or embolus, the balloon is inflated, and the catheter with enlarged balloon is withdrawn. In this procedure, the enlarged balloon pushes the thrombus or embolus out of the vessel as the catheter is withdrawn.

In an angioplasty procedure, the balloon of the catheter is inflated in proximity to athroscorotic plaque. In this common procedure, the pressure of the balloon forces the plaque against the vessel walls hereby enlarging the flow path through the vessel. These and other techniques benefiting from balloon catheter technology are disclosed in the following patents which are incorporated herein by reference:

| U.S. Pat. No. | Inventor |
| --- | --- |
| 3,438,375 | R. Ericson |
| 3,866,599 | C. Johnson |
| 4,217,903 | R. Witherow |
| 4,254,774 | J. Boretos |
| 4,823,812 | U. Eshel |
| 4,913,701 | A. Tower |
| 5,036,868 | A. Berggren |

In all of these procedures, the initial diameter of the catheter is of particular interest. This elongate flexible structure is typically introduced through long, sometimes torturous, conduits in order to reach the operative site. In some cases, these conduits are quite narrow so that the diameter of the catheter is of critical importance. Such is the case with arteries in the hand of a patient. An embolectomy procedure performed in these environments might require a catheter having a diameter as small as 1 French.

The problem with achieving catheter diameters of this size has been significantly compounded in the case of balloon catheters. With these devices, the balloon structure has typically been provided on the outside of the catheter thereby increasing the diameter of the device. An inflation hole extends through the catheter wall into an inflation lumen of the catheter. The balloon with a cylindrical configuration is disposed over this hole and wound on the catheter body to form a seal on either side of the hole. By pressurizing the inflation lumen, an inflation fluid passes through the hole to inflate the balloon beyond the outer surface of the catheter body.

Attempts have been made to reduce the overall thickness of this balloon structure. The catheter wall has been thinned so that the diameter of the balloon windings can be formed in a recess. This has weakened the catheter walls so that the balloon windings tend to compress the lumen of the catheter. In some instances, metal bushings have been placed over the recess to prevent the collapse of the catheter walls. In such a combination, the total thickness of the catheter is determined by the thickness of four separate structural elements, the catheter wall, the bushing, the balloon and the winding. Since each of these elements has a cylindrical configuration, the wall thickness of each element is doubled in defining the diameter of the total construction. Thus, the catheter body provides two wall thicknesses in the overall diameter of the catheter. Similarly, the bushings, the balloon, the windings and any glue associated with the winding structure each add two thicknesses of material to the diameter of the catheter. As a consequence, eight layers of material have typically contributed to the overall thickness of the catheter.

In spite of the many disadvantages relating to the overall size of such catheters, the methods for constructing the catheter have demanded this configuration. The catheter body has typically been extruded, and any recesses provided in the catheter wall have been machined along with the inflation hole. Bushings have been placed over the recesses. The balloon in the initial form of a cylindrical elastic material has been positioned across the inflation hole and the balloon has been stretched and wound over the bushings. Gluing these windings in place has completed formation of the balloon structure.

Based on this method, typical of the prior art, the entire balloon structure has been formed on the exterior of the catheter body because of its accessibility. The detrimental effect on the overall diameter of the catheter has been accepted without recourse, but it has necessarily limited any possibility of providing balloon catheters in sizes smaller than 2 Fr.

SUMMARY OF THE INVENTION

In accordance with the present invention, an elongate catheter body is provided with an inflation lumen. Importantly, the balloon material is disposed interiorly of the catheter body in the inflation lumen. This material is restrained around a balloon hole which extends through the wall of the catheter into the inflation lumen. The balloon hole may be provided at the distal end of the catheter or in the side wall of the catheter body. When the inflation fluid is introduced into the inflation lumen, the balloon material expands through the balloon hole, outwardly of the catheter body.

When the catheter is initially inserted, the balloon material is disposed interiorly of the catheter body so that the maximum diameter of the catheter is dictated solely by the outside diameter of the catheter wall. There need be no bushings, windings or glue on the outside of the catheter wall to increase this diameter. In its thinnest configuration, the entire catheter structure can be formed with only three thicknesses of material, two thicknesses resulting from the cylindrical catheter wall and a single thickness of elastic material restrained around a side hole in the catheter.

With only three wall thicknesses, as opposed to the eight wall thicknesses of the prior art, significantly smaller diameters of catheters can now be formed making this important technology available in many new areas of the body anatomy.

These and other features and advantages of the present concept will be more apparent with a description of preferred embodiments and the best mode of the invention, and reference to the associated drawings.

DESCRIPTION OF THE DRAWINGS

FIG. 1 is a side view, partially in section, of one embodiment of a balloon catheter of the present invention;

FIG. 2 is an axial cross-section view similar to FIG. 1 showing an additional embodiment of the present invention;

FIG. 2a is a cross-section view taken along lines 2a–2a of FIG. 2;

FIG. 3 is an axial cross-section view similar to FIG. 2 of a further embodiment of the present invention;

FIG. 3a is a radial cross-section view taken along lines 3a–3a of FIG. 3.

FIG. 4 is an axial cross-section view of a further embodiment of the invention which can accommodate introduction of an injectate through the catheter;

FIG. 10 is a side view similar to FIG. 1 and illustrating a spiral balloon configuration;

FIG. 11 illustrates a step in a preferred method of manufacture where a mandrel is dipped into an elastomeric material;

FIG. 12 illustrates a further step of the method where the coated mandrel is inserted into a catheter body;

FIG. 13 is a front elevation schematic view of a coextruder adapted for use in a further method of manufacture;

FIG. 13a is a top plan view of the coextruder illustrated in FIG. 13;

DESCRIPTION OF PREFERRED EMBODIMENTS

Figure 5:
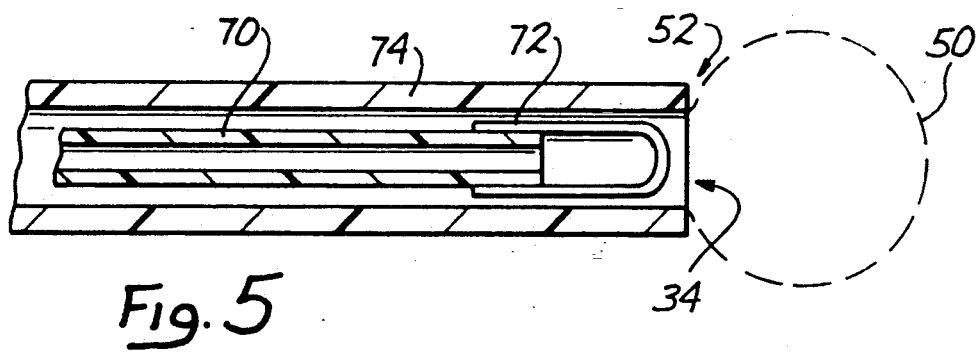
FIG. 5 is an axial cross-section view of a further embodiment of the invention including an outer sheath.

A catheter is illustrated in FIG. 1 and designated generally by the reference numeral 10. This catheter 10 includes a balloon structure 12 and is representative generally of any elongate medical instrument which is insertable through a body cavity or conduit to provide an inflatable structure at a distal location. Such instruments may include not only catheters but also endoscopes.

In the case of a catheter, a balloon structure is known to provide advantages in both embolectomy and dilatation procedures. In an embolectomy procedure, the catheter is inserted into a vessel and guided so that its distal tip extends beyond an embolus or thrombus. At this location a distal balloon is inflated to fully occupy the interior lumen of the vessel. As the catheter is withdrawn through the incision in the vessel, the balloon pushes the embolus or thrombus thereby removing it from the vessel.

In dilatation procedures, the catheter is inserted into a conduit, such as the urethra, and inflated to push the conduit walls outwardly thereby enlarging or dilating the conduit. In one type of dilatation procedure atherosclerotic plaque coats the interior walls of a vessel and blocks blood flow. In this procedure, the catheter is inserted into the vessel to the point where the blockage occurs. At this location, the balloon is inflated pressing the plaque against the vessel walls thereby dilating the vessel. In all of these cases, the balloon structure provides means for producing a pressure or force exteriorly of the body to perform some function at an operative site within a body conduit.

The catheter 10 will typically include an elongate catheter body 14 having some degree of flexibility. The body 14 is typically formed along an axis 16 which extends between a proximal end 18 and a distal end 21 of the catheter 10. A hub 27 is disposed at the proximal end 18 of the catheter 10 and may include at least one Luer fitting 30. The fitting 30 permits attachment of the catheter 10 to various external systems, such as a source of inflation pressure (not shown).

The catheter body 14 will typically take the form of an elongate cylinder having an outer wall 36 which at least partially defines an inflation lumen 38 that extends from the hub 27 to the balloon structure 12. In many catheters, the inflation lumen 38 will merely be one of several lumens which perform various functions in a particular embodiment of the catheter 10. The opening 34 is configured such that it extends through the catheter wall 36 providing a passage from the inflation lumen 38 through the wall 36 to regions exterior of the catheter 10.

In a preferred embodiment, the balloon structure 12 includes a membrane 41 of elastomeric material, and means for retaining that membrane 41 around the opening 34. In the form illustrated in FIG. 1, this retention means include a bead of glue 43 which fixes the membrane 41 to the catheter wall 36 and any other portions of the catheter body 10 which define the opening 34. The retention means may form a seal around the opening 34 but these sealing characteristics may not be required in a particular embodiment.

In the embodiment illustrated in FIG. 1, the membrane 41 forms a balloon 45 which is operable between a deflated state (shown by the solid lines 47 in FIG. 1) and an inflated state (shown by the dotted lines 50 in FIG. 1).

The balloon structure 12 can be located anywhere along the catheter body 14 but will typically be disposed at the distal end 21 in proximity to an opening 34 in the catheter body 14. In the embodiment illustrated in FIG. 1, this opening 34 is located at the end of the catheter body 14 where the opening 34 is formed in a radial plane and faces axially of the catheter 10. In other embodiments, the opening 34 may be formed in the side of the catheter body as illustrated in FIG. 2.

It is of particular importance to the present invention that in the deflated state, the balloon structure 12 is disposed entirely within the circumferential dimension defining the outer surface of the catheter wall 36. There is no balloon membrane or other elastomeric material or any retention adhesive or windings which exceed this diameter of the catheter wall 36. In the illustrated embodiment, the balloon structure 12 is disposed entirely within the inflation lumen 38 where the bead of glue 43 retains the membrane 41 circumferentially of the lumen 38.

In operation, a source of inflation pressure (not shown) is coupled to the Luer fitting 30 and a pressurizing medium, such as saline, is introduced into the inflation lumen 38. As this inflation medium is pressurized, the membrane 41 associated with the balloon 45 expands through the opening 34 to the inflated state shown by the dotted lines 50. When the inflation medium is withdrawn or depressurized, the elastomeric characteristics associated with the membrane 41 cause it to retract back from the enlarged inflated configuration.

When the balloon 45 is initially inflated, the inflation pressure forces it against the catheter wall 36 forming a seal around the circumference of the opening 34. This seal, designated by the reference numeral 52, may form regardless of any sealing characteristics which may be associated with the retention means, such as the bead of glue 43.

In the embodiment of FIG. 2, the distal end 21 of the catheter body 14 is closed by an end cap 56 which can be molded with, glued to, or otherwise attached to the catheter wall 36. As previously noted, the opening 34 in this embodiment is formed in the side of the catheter body 14 where it extends radially of the catheter wall 36 and faces laterally of the catheter 10.

As in the previous embodiment, the membrane 41 is retained to the catheter wall 36 around the opening 34 and interiorly of the inflation lumen 38. In this particular case, the membrane 41 will have a more planar configuration in axial cross-section than the balloon 45 in the FIG. 1 embodiment. Nevertheless, as the inflation lumen 38 is pressurized, the membrane 41 will expand outwardly through the opening 34 to form the inflated balloon 50. As in the previous case, the inflated balloon 50 will extend in the same direction as the opening 34 which in the case of the FIG. 2 embodiment is laterally of the catheter 10.

The embodiment of FIG. 2 is of particular interest since it provides potentially the most narrow configuration for the catheter 10. In this particular embodiment, the cross-section of the catheter includes only three layers of material. Two of the layers result from the catheter wall 36 but only a single layer of the membrane 41 is required for this embodiment. In contrast, it will be noted that the embodiment of FIG. 1 includes four layers of material, two each associated with the catheter wall 36 and the membrane 41.

With reference to FIG. 2A it will be apparent how this reduced thickness is achieved. As illustrated, the bead 43 which retains the membrane 41 to the catheter wall 36 is formed on only one side of the axis 16. It follow that along any cross-sectional diameter of this embodiment, there is only a single thickness of the membrane 41. Nevertheless, this embodiment forms a fully inflatable balloon 50 as long as the bead 43 fully circumscribes the opening 34.

In the further embodiment of FIG. 2, a lateral balloon such as that illustrated in FIG. 2 can be formed with a radially glue bead 43 similar to that illustrated in FIG. 1. In this case, the opening 34 is formed laterally of the axis 16 as in the FIG. 2 embodiment, but the membrane is provided with the more spherical configuration as in the FIG. 1 embodiment. Although the membrane 43 does not closely circumscribe the opening 34, it is nevertheless attached to those portions of the catheter wall 36 that define the opening 34. This embodiment benefits from ease of manufacture as will be more apparent from the following discussion of manufacturing techniques.

The radial glue bead 43 may be closely spaced to the opening 34 as illustrated in FIG. 3 or it may be distantly spaced from the opening 34 as illustrated in FIG. 4. The only requirement for this relationship between the radial bead 43 and the opening 34 is that the bead 43 be disposed proximally of the opening 34. In the embodiment of FIG. 4 an injection port 61 is provided between the glue bead 43 and the opening 34. This port 61 provides access to lumen 38 and facilitates introduction of an injectate into the catheter 10 and outwardly through the opening 34.

This introduction of an injectate would most easily be accomplished with the balloon 45 in the deflated state shown by the solid lines 47. In this state, the injectate entering the port 61 would be forced between the membrane 41 and the catheter walls 36, as shown by the arrow 63, to exit the catheter 10 through the opening 34.

In the embodiment of FIG. 5, a more conventional catheter is illustrated to include a catheter wall 70 and a balloon 72 which is glued or wound on the outside of the catheter wall 70. In this case, a sheath 74 is provided to enclose the catheter wall 70 as well as the balloon 72. The opening 34 is provided in the sheath 74. As the balloon 72 is inflated (through a lumen formed by the catheter wall 70) it is restricted in all directions by the sheath 74 except in the area of the opening 34. As a result, the balloon 72 expands through the opening 34 forming the seal 52 with the sheath 74. It is apparent that a lateral balloon could also be formed by a lateral opening 34 similar to that illustrated in FIG. 2.

Figure 6:
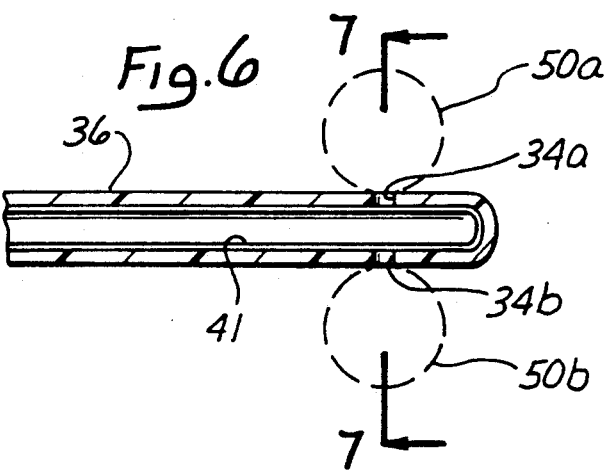
FIG. 6 is an axial cross-section view of an embodiment adapted to form more than one radially spaced balloon.
Figure 7:
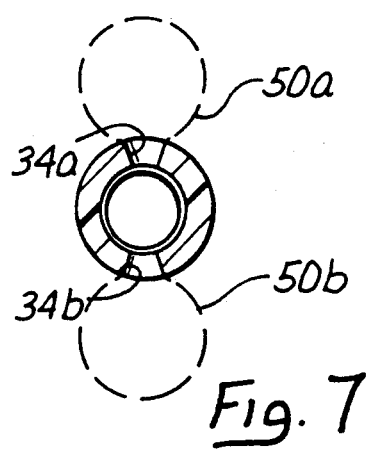
FIG. 7 is a cross-sectional view taken along lines 7—7 of FIG. 6.

In a further embodiment of the invention, multiple balloons can be formed by providing more than one opening 34 in the catheter wall 36 or sheath 74. The embodiments of FIGS. 6 through 10 are representative of such multiple balloon configurations. In FIG. 6, a pair of radially spaced openings 34a and 34b are formed in the catheter wall 36. In the manner previously discussed, the application of pressure to the inflation lumen 38 results in inflating the membrane 41 through the openings 34a and 34b to form the respective inflated balloons 50a and 50b. These balloons 50a, 50b are radially spaced as best shown in FIG. 7.

Figure 8:
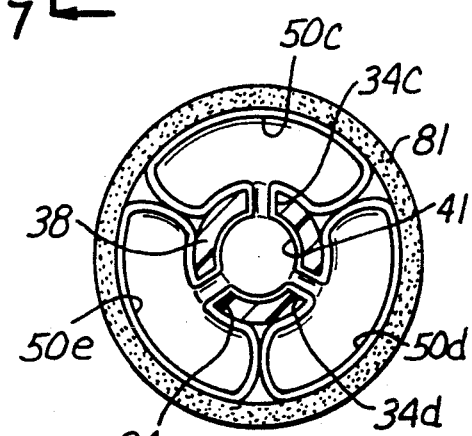
FIG. 8 is a cross-sectional view similar to FIG. 7 and illustrating a multiple balloon embodiment providing a full circumferential balloon structure.

Multiple balloons can also be radially spaced to form a single balloon structure that fills the entire circumference around the catheter 10. Such an embodiment is illustrated in FIG. 8 wherein the balloon structure 12 includes three separate balloons 50c, 50d, and 50e formed from a single membrane 41 deployed through respective openings 34c, 34d, and 34e. The resulting balloon configuration provides a substantially constant pressure radially outwardly around the entire circumference of the catheter 10. This embodiment will be of particular interest in dilatation and embolectomy procedures which are typically conducted in a blood vessel, such as that designated by the reference numeral 81.

Figure 9:
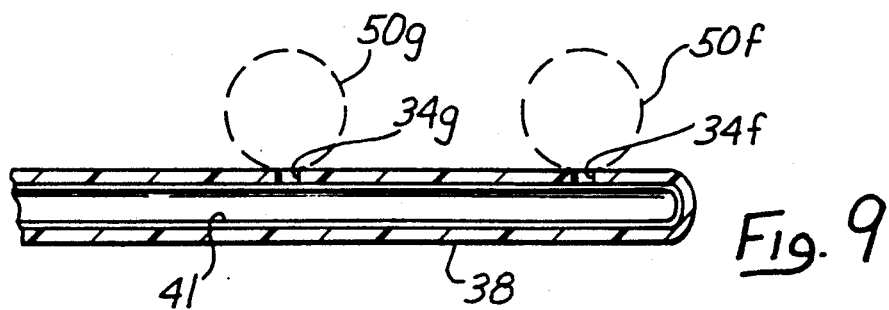
FIG. 9 is an axial cross-section view similar to FIG. 6 but illustrating multiple balloons axially spaced.

In the same manner that the balloons 50a–50e are radially spaced, the balloons can also be axially spaced as illustrated in FIG. 9. In this case, a pair of balloons 50f and 50g can be inflated through the respective openings 34f and 34g. Of course various combinations of radially and axially spaced balloons will now be apparent. For example, two of the triple balloon structures illustrated in FIG. 8 could be axially spaced as illustrated in FIG. 9 to provide a substantially constant circumferential pressure at two axial locations.

The embodiment of FIG. 10 illustrates that the openings 34 can be substantially any shape, not just the circular configuration previously discussed. In FIG. 10, the opening is longitudinal in configuration and spirally oriented with respect to the catheter body 14. This opening is divided by several bridges 85 which divide the opening into segments 34h, 34i and 34j. These bridges 85 may be desirable to increase the column strength and structural rigidity of the catheter 10. With the openings divided into segments 34h through 34j, the resulting balloon is also segmented into spiral balloon portions 50h, 50i, and 50j respectively. As with the embodiments of FIGS. 6 through 9, the multiple balloons 50h–50j can be formed from a single membrane 41.

The methods for manufacturing the foregoing embodiments of the concept are quite diverse. The embodiment of FIG. 5 can be most easily manufactured since a large portion of this embodiment is a conventional catheter construction including the catheter wall 70 and the balloon 72 which is wound on the outer surface of the catheter wall 70. This structure is then inserted into the sheath 74 which has been appropriately apurtured to form the opening 34 either laterally or axially of the sheath 74.

Embodiments of the invention which require an elastomeric tube within an outer tube, such as the embodiments of FIGS. 1 and 3 through 10, can be formed in several manners. As illustrated in FIG. 11, a mandrel 81 can be provided with a diameter generally equivalent to the diameter desired for the inflation lumen 38. The length of the mandrel 81 should be such that it can extend from the proximal end 18 of the catheter body 14 to the distal end 21.

A vessel 83 containing the elastomeric material desired for the membrane 41 can be provided and heated to give the material 41 fluid characteristics. Then the distal end of the mandrel 81 can be dipped in the heated material of the membrane 41 to form a coating on the mandrel. This coating can be partially cured to provide it with a more solid configuration for the balloon 45.

Of particular importance to this process is the axial insertion of the coated mandrel 81 into the catheter body 14 as illustrated in FIG. 12. This catheter body 14 can be formed in accordance with conventional extrusion methods. After the balloon 45 is in place, the mandrel 81 can be removed leaving the balloon 45 within the catheter body 14. The step of withdrawing the mandrel 81 can be facilitated by initially coating the mandrel with a release agent so that it can be easily removed, leaving the balloon 45 in place.

This method may be preferred since the end of the balloon 45 is automatically formed in the dipping step of the process. No additional action need be taken in order to close the inflation lumen of the balloon 45. However, as a final step in this process, the distal end of the catheter body 14 will need to be closed if an lateral opening 34 is contemplated. This closure of the catheter body 14 can be accomplished by melting and molding the catheter material over the distal end of the catheter body or otherwise preforming a distal tip and attaching the tip, such as the end cap 56, to the catheter body 14.

A coextrusion process can also be used to form an elastomeric tube within the catheter body 14. As illustrated in FIG. 13, the materials associated with the catheter body 14 and the membrane 41 can be loaded into respective hoppers 83 and 85, heated, and forced by way of respective screws 87, 90 into a crosshead 92. The crosshead 92 is configured in accordance with known techniques to extrude an inner tube from the material in the hopper 85 and an outer tube from the material in the hopper 83. The result is a tubular membrane 41 within a more rigid catheter body 14. This coextrusion can be cut to length and the distal end formed to produce the embodiments of FIGS. 3 and 4. In this process the elastic membrane 41 can to be closed at the distal end in order to form the balloon 45. If a lateral opening 34 is provided, the distal end of the catheter body 14 also can be closed in accordance with methods previously discussed.

If a particular method can accommodate formation of the opening 34 prior to inserting or otherwise forming the elastic membrane 41 within the outer tube 14, this is desirable. For example, in the method of FIG. 12, the lateral opening 34 can be formed prior to insertion of the coated mandrel 81.

If the prior formation of the opening 34 is not possible, that opening needs to be carefully formed in the catheter wall 36 without puncturing the membrane 41. This can be most easily accomplished using a laser 96 which can be carefully operated to control the depth of the cut. By limiting this depth to the thickness of the catheter wall 36, any cutting of the membrane 41 can be avoided.

Figure 15:
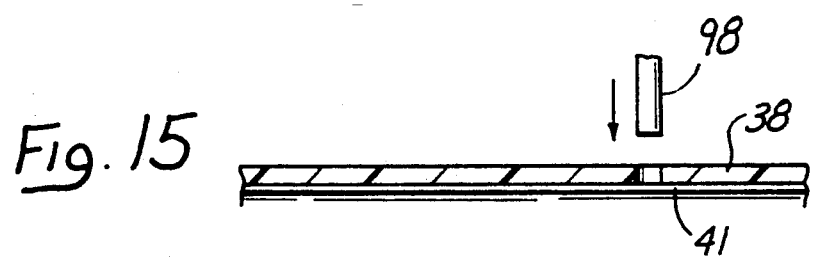
FIG. 15 illustrates a method step similar to FIG. 14 wherein a flat point drill is used to form the inflation opening.

Another alternative for cutting the catheter wall 36 without penetrating the membrane 41 is to mechanically drill the catheter wall 36 with a flat end drill bit 98, as illustrated in FIG. 15.

Figure 14:
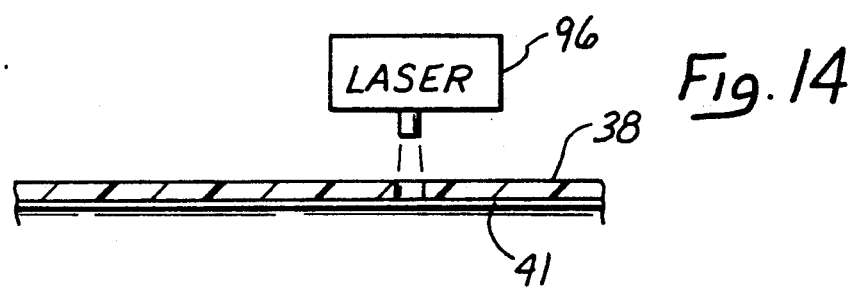
FIG. 14 illustrates a method step whereby a laser forms an inflation opening in a catheter body.
Figure 16:
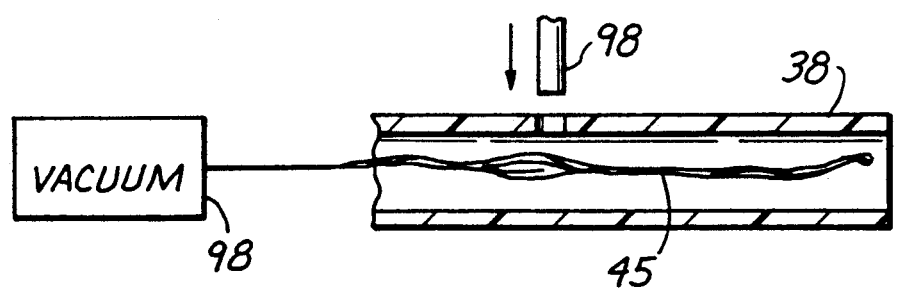
FIG. 16 illustrates a method step wherein a vacuum is applied to the inner balloon structure to separate the balloon from the catheter wall prior to formation of the inflation opening.

This cutting either by the laser 96 or the drill bit 98 can be further facilitated by use of a vacuum 98 to draw the balloon 45 into a collapsed configuration as illustrated in FIG. 16. This will withdraw the balloon 45 from proximity to the catheter wall 36 so that the cutting steps illustrated in FIGS. 14 and 15 need not be as carefully controlled.

The materials associated with the present invention are of particular interest not only to facilitate their functions in a preferred embodiment of the catheter 10, but also to enable the foregoing processes of manufacture. In general the materials associated with the catheter body 14 and the membrane 41 can be any thermoplastic or thermoset material. Depending on the process of manufacture, these materials are formable in that they can be molded. Some of these materials are also extrudable which facilitates the process illustrated in FIGS. 13 and 13a. In most embodiments, both the catheter body 14 and the membrane 41 will be flexible although rigid and semi-rigid configurations may also benefit from the concept.

The material associated with the membrane 41 will typically be more flexible than the material associated with the body 14 which is relied on for additional column strength. The durometer of the material forming the body 14 will preferably be in a range from Shore 5A to Shore 100D. A range of particular advantage occurs from a Shore hardeess of 35D to 100D.

In comparison, the material forming the membrane 41 will preferably have a durometer between Shore 5A and Shore 100D. A preferred range of durometer might be between Shore 25A and Shore 100D. Regardless of the durometer of the material, the flexibility of the catheter 10 is of primary consideration. In embodiments wherein the wall thicknesses of the body 14 and the membrane 41 are quite small, higher durometers such as Shore 50D may still provide the desired flexibility.

The thermoplastic and thermoset materials which are of particular interest for the body 14 include rubbers, elastomers, silicones and polycarbonates. Materials of interest for the membrane 41 include rubber, elastomers including urethanes, polyethylene, polyethyleneterethalate, polyvinylchloride, silicone, nylon and latex.

In a preferred embodiment the catheter body is formed from Hytrel, a trademark of DuPont de Nemours. This material is coextruded with an outside diameter of about 1 Fr. to 10 Fr. and an inside diameter of about 0.005-0.100 inches. The membrane 41 is coextruded from Craton, a trademark of Shell Oil Company. The membrane 41 is coextruded in juxtaposition to the inner surface of the catheter body 14. An inflation lumen of about 0.003-0.080 inches diameter is formed in this particular embodiment so that the membrane 41 has the thickness of about 0.001 to 0.020 inches.

Beyond these considerations, the materials forming the catheter body 14 and the membrane 41 can be selected for their compatibility with each other. Generally it is felt that the materials are compatible if the membrane 41 does not automatically adhere to the material forming the catheter body 14. This permits the membrane 41 to freely move relative to the catheter wall 38 so that it can stretch through and beyond the opening 45 to form the expanded balloon 50. If it is preferrable to use materials which are not compatible in this sense, a release agent can be coextruded or applied to the balloon 45 on the dipped mandrel 81. Such a release agent would typically provide the characteristics required for these otherwise incompatible materials.

Many variations in the concept of this invention will now be apparent to those skilled in the art of balloon catheter design. Certainly different materials can be contemplated for the membrane 41 as well as the catheter body 14. Similarly, steps in the manufacturing processes can be altered all within the skill of the art. Many different embodiments of the invention can be formed by adjusting the various positions for the opening 34 as mentioned with respect to the examples of FIGS. 6-10.

It will also be noted that in a particular catheter construction, multiple lumens can be formed each with its own membrane 41 or balloon 45 which would be independently inflatable and deflatable to achieve the advantages of the present concept. In such an embodiment, multiple balloons could be provided around the circumference of the catheter body 14 in the manner illustrated in FIG. 7. By independently inflating each of the balloons around the circumference, the distal tip of the catheter could be guided in a direction opposite to the inflated balloon. In such an embodiment, the catheter could function not only for embolectomy or dilatation purposes, but also as a guiding catheter.

Given the wide variety of substitutions, all within the breadth of this concept, the broad scope of the invention should not be limited to the drawings and the described embodiments, but should be ascertained only with reference to the following claims.

We claim:

1. A balloon catheter, comprising:
   a catheter body extending along a longitudinal axis between a proximal end of the catheter body and a distal end of the catheter body;
   an outer wall included in the catheter body and defining at least one lumen extending longitudinally of the catheter body;
   first portions of the outer wall included in the catheter body and defining an opening from the lumen outwardly of the catheter body;
   an expandable material including a peripheral edge portion and a central portion and being mounted in the catheter body with the central portion extending distally of the peripheral edge portion;
   retention means spaced proximally of the opening for permanently securing the peripheral edge portion of the expandable material to the catheter body;
   inlet means for admitting a pressurizing fluid into the lumen;
   the expandable material being inflatable upon entry of said pressurizing fluid into the lumen, from a deflated state wherein the central portion is disposed entirely within the lumen, to a inflated state wherein the central portion extends through the opening to form a seal with the wall portions, and beyond the catheter wall to form a balloon exteriorly of the catheter body; and
   second portions of the outer wall defining an injection port between the retention means and the opening for introducing an injectate into the catheter and outwardly through the opening.

2. The balloon catheter recited in claim 1, wherein the outer wall includes an outer surface and an inner surface; and
   the retention means is disposed on the inner surface of the outer wall.

3. The balloon catheter recited in claim 1 wherein the first portions of the outer wall define the opening axially of the catheter body at the distal end of the catheter body.

4. The balloon catheter recited in claim 1 wherein the expandable material comprises an elongate tube having a proximal end and being sized and configured for disposition in the lumen of the catheter body, the peripheral edge portion of the expandable material being disposed at the proximal end of the tube.

5. The balloon catheter recited in claim 1 wherein the inlet means is a first inlet means for admitting a pressurizing fluid into the lumen and the catheter further comprises second inlet means for admitting an injectate into the injection port, distally through the lumen, and outwardly through the opening.

* * * * *

UNITED STATES PATENT AND TRADEMARK OFFICE
CERTIFICATE OF CORRECTION

PATENT NO. : 5,295,960
DATED : March 22, 1994
INVENTOR(S) : Wassim Aliahmad, Said S. Hilal It is certified that error appears in the above—identified patent and that said Letters Patent is hereby corrected as shown below:

Col. 6, line 15, after the word "to" add the word --inflation--.

Signed and Sealed this

Twentieth Day of September, 1994

Attest:

BRUCE LEHMAN

Attesting Officer     Commissioner of Patents and Trademarks